US005660990A

United States Patent [19]
Rao et al.

[11] Patent Number: 5,660,990
[45] Date of Patent: Aug. 26, 1997

[54] SURFACE IMMOBILIZATION OF MAGNETICALLY COLLECTED MATERIALS

[75] Inventors: Galla Chandra Rao, Princeton, N.J.; Paul A. Liberti, Huntingdon Valley, Pa.

[73] Assignee: Immunivest Corporation, Wilmington, Del.

[21] Appl. No.: 516,694

[22] Filed: Aug. 18, 1995

[51] Int. Cl.⁶ ............... C12Q 1/68; C12Q 1/70; G01N 33/53

[52] U.S. Cl. .................. 435/6; 435/5; 435/91.2; 435/7.1; 435/7.25; 435/7.9; 435/261; 436/526; 436/501; 436/518; 436/807; 436/824; 209/214; 209/217; 536/24.3; 530/388.1

[58] Field of Search ................... 435/6, 5, 91.2, 435/91.1, 7.1–7.9, 2, 4, 261; 536/24.3, 24.33; 436/526, 501, 518, 807, 824; 535/372; 209/214, 217

[56] References Cited

U.S. PATENT DOCUMENTS

| | | |
|---|---|---|
| 4,247,406 | 1/1981 | Widder et al. . |
| 4,267,235 | 5/1981 | Rembaum et al. . |
| 4,335,094 | 6/1982 | Mosbach .................. 424/1 |
| 4,343,901 | 8/1982 | DeFilippi . |
| 4,376,110 | 3/1983 | David et al. . |
| 4,446,232 | 5/1984 | Liotta . |
| 4,517,288 | 5/1985 | Giegel et al. . |
| 4,628,037 | 12/1986 | Chagnon et al. .......... 436/526 |
| 4,672,040 | 6/1987 | Josephson ................. 436/526 |
| 4,752,562 | 6/1988 | Sheiman et al. . |
| 4,774,174 | 9/1988 | Giegel et al. . |
| 4,786,606 | 11/1988 | Giegel et al. . |
| 4,795,698 | 1/1989 | Owen et al. . |
| 4,906,439 | 3/1990 | Grenner . |
| 4,925,788 | 5/1990 | Liberti . |
| 4,935,147 | 6/1990 | Ullman et al. ............. 210/695 |
| 4,965,007 | 10/1990 | Yudelson . |
| 4,985,166 | 1/1991 | Leising et al. ............. 252/62.54 |
| 4,988,618 | 1/1991 | Li et al. . |
| 5,071,774 | 12/1991 | Vorpahl et al. ............ 436/501 |
| 5,108,933 | 4/1992 | Liberti et al. . |
| 5,126,242 | 6/1992 | Hachmann et al. . |
| 5,169,754 | 12/1992 | Siiman et al. . |
| 5,186,827 | 2/1993 | Liberti et al. . |
| 5,200,084 | 4/1993 | Liberti et al. . |
| 5,206,159 | 4/1993 | Cohen et al. . |
| 5,238,811 | 8/1993 | Fujiwara et al. . |
| 5,240,640 | 8/1993 | Siiman et al. ............. 252/315.2 |
| 5,242,837 | 9/1993 | Slovacek et al. . |
| 5,283,079 | 2/1994 | Wang et al. . |
| 5,318,914 | 6/1994 | Matte et al. ............... 435/526 |
| 5,364,796 | 11/1994 | Blackwood et al. . |
| 5,466,574 | 11/1995 | Liberti et al. ............. 435/5 |
| 5,536,644 | 7/1996 | Ullman et al. ............ 435/7.25 |
| 5,602,042 | 2/1997 | Farber et al. ............. 436/526 |

*Primary Examiner*—W. Gary Jones
*Assistant Examiner*—Dianne Rees
*Attorney, Agent, or Firm*—Dann, Dorfman, Herrell and Skillman

[57] ABSTRACT

A method for determining the presence and/or concentration of a target substance e.g. protein, nucleic acid, bioparticle etc. in a fluid sample is provided. The method disclosed combines elements of immunoassays, coated cup assays and magnetic particle separation to effect the quantitation and recovery of an analyte in solution. Also the method ensures the non-reorientation of magnetically collected material by linking the magnetic particles to a collection surface via a specific binding pair. This linkage immobilizes the magnetic-analyte-containing material and thus allows for vigorous washing and reagent addition without significant redistribution or displacement. Thus the assay of this invention offers the speed of diffusion controlled kinetics as in a ferrofluid assay, the speed of collection of labeled target substance as in a magnetic assay as well as the ability to magnetically monolayer the ferrofluid, all of which is combined with the ease of washing and signal detection found in a coated cup assay.

39 Claims, No Drawings

SURFACE IMMOBILIZATION OF MAGNETICALLY COLLECTED MATERIALS

FIELD OF THE INVENTION

The present invention is directed to a method of immobilization of magnetically collected material. This method of immobilization is useful in a variety of applications, including immunoassay, nucleic acid detection, drug testing, gene therapy, in-vitro fertilization, cell analysis and food testing. The invention described herein enables the determination of the concentration of an analyte of biological or medical significance with improved precision due to an increased signal to noise ratio at the low end of analyte concentration and an increased total signal at the high end of analyte concentration. The improved assay combines elements of a magnetic immunoassay together with elements of a coated cup-type assay.

BACKGROUND OF THE INVENTION

Magnetic gradients have been used to separate magnetically responsive material from non-magnetically responsive materials for hundreds of years. Historically, the major industrial application was in the field of mining, from which derive some of the oldest inventions and basic patents. Magnetics have evolved as applied to separations, as well as in numerous other well-known applications, such as the magnetic recording industry, the medical sciences, electronics and other industrial uses.

The science of separations involving the isolation of molecules has evolved independently. Separations initially involved principles of solubility, advancing to methods based on gross physical properties of molecules, such as size and shape. With the introduction of chromatography, separation techniques were developed based initially on chemical interactions which were not well defined. This approach generally led to employing surface charge density as a basis for one form of separation. These and other methods based on similar principles achieved separation typically on the basis of one property or characteristic of a molecule and it became, and in many instances still is, customary to employ several techniques sequentially in order to isolate some specific compound of interest from a complex mixture.

With the emergence of modern biological science, the principle of affinity reactions (recognition at the molecular level via molecular "locks" and "keys") became known and was embodied in technology such as immunoassay, DNA/RNA hybridization techniques and, more recently, mammalian cell isolation. In such methods where a separation is performed, means for retrieving the bound element of a binding pair reaction (lock or key) was required. Methods involving "anchoring" one element evolved from simple, physically removable surfaces to various beads which could be retrieved by centrifugation. With this evolution came the appreciation that small beads have higher surface to mass ratios and that other forces, such as magnetics, could be conveniently used for separation.

In order for magnetic particle-based separation technology to become a reality, materials had to be developed with a property commonly referred to as superparamagnetism, which is the property whereby a magnetic particle exhibits a magnetic dipole while in a magnetic field and loses the dipole upon removal of the field. This property allows such materials to be resuspendable following a magnetic collection, which is essential for most separation applications. Given the various developments which had to occur, it is only in the last three decades or so that magnetic separations have been introduced into medical science and technology as a means for selecting out of complex mixtures material to be examined or analyzed, or alternatively as a means for performing a "bound/free" separation, as in the case of immunoassay. In view of the wide-scale use of magnetics in this and other clinically relevant testing, this step is critical for almost all such applications. With the extensive use of automation, it has become clear that there is a considerable need for improvement as regards the collection of magnetic materials. The present invention addresses this need.

Immunoassays are widely used in the clinical laboratory for determining the concentration of an analyte of biological or medical significance. The principles of immunoassays are reasonably well understood. Generally speaking, there are two categories of immunoassays: competitive assays and sandwich assays. For low molecular weight analytes such as drugs or metabolites, it is customary to perform competitive immunoassays. Typically, a fixed, limited quantity of specific antibody is allowed to incubate with a known concentration of labeled analyte and test sample containing some unknown concentration of the analyte of interest. The quantity of label bound to antibody is inversely proportional to the amount of analyte in the test sample. For quantitation, it is customary to perform a bound/free separation so that labeled analyte associated with the antibody can be detected. Assays which employ such a separation are termed heterogeneous. There are numerous ways for performing the bound/free separation which include adsorbing or covalently linking specific antibody to the inside of a tube (coated tube assay) or onto beads which can either be centrifuged or separated with filters or by magnets. Typically, a separation system should have the characteristics that the separation can easily be performed, excess reagent can be removed simply and non-specifically bound analyte can be washed free of the immobilized antibody with its specifically bound, labeled analyte. For analytes which have at least two characteristic antigenic determinants, a simpler and more precise approach is to perform a sandwich immunoassay, which uses two antibodies. One of the antibodies is directed to one antigenic binding site as a capture antibody while the other antibody is directed at the second binding site as the signal generating antibody. Thus, if the capture antibody is separated from solution, or bound on some solid support, the only way in which signal generating antibody can be bound to solid support or separated from solution is via binding to analyte. The advantages of sandwich assay are that: (1) signal is directly proportional to analyte concentration on the low end of the analyte curve; (2) extreme sensitivity can be obtained on the low concentration end; (3) sandwich assays are assays of "excesses" since capture antibody and label antibody are typically in excess of analyte, and so error is mainly related to accuracy of sample input; and (4) a wide dynamic analyte detection range (as much as 4–5 logs) is possible. Sandwich assay techniques, like competitive assays, employ a wide range of systems for performing bound/free separations.

Considerable effort has been devoted to the development of assays capable of being performed as quickly and as simply as possible. Several inventions are based on the principle of covalently attaching a fixed quantity of antibody to a well-defined region on a solid support where the latter has reasonable capillary action. See, for example, U.S. Pat. Nos. 5,126,242; 4,517,288; 4,786,606; 4,774,174; 4,906,439; 5,364,796; 4,446,232; and 4,752,562. Typically in such assays, specimen and labeled analyte are placed with great precision on such a solid support so as to permit competitive binding on the bound antibodies to occur. Next, solution is added which causes unbound labeled analyte to be carried from the binding region via capillary action. If the analyte is enzyme labeled, and if the liquid employed to "chromatograph" away unbound labeled analyte contains excess substrate, then a color is developed which will be proportional to the quantity of enzyme specifically bound. Another type of assay operates on a different principle, which effects "bound/free" separation by positioning solid phase antibody in some fraction of the total volume of the system. If the fractional volume in which specific binding takes place can be partitioned from the remainder of the system, then it will be possible to quantitate bound signal in the presence of an equilibrium quantity of "free" analyte, but the amount of "free" analyte in the detection region will be reduced by the volume element of the immobilized antibody regions divided by the total volume of the system. Such assays are referred to as "curtain assays" as this large fraction of unbound analyte and signal is effectively hidden behind a curtain.

Each of the above-described analytical systems suffers from its own peculiar deficiencies. In the case where capillary action is employed to chromatograph away unbound signal, non-specific binding of signal producing agent to the matrix can result in substantial background. In the case where signal producing agent includes labeling antibody or some part thereof as in the case of sandwich assays, non-specific binding becomes a significant concern. Thus, sandwich assays where medium to high sensitivity is required cannot be performed. In the curtain type assays, there is a finite limit on the smallness of the fractional volume where antibody can be bound. Hence, free signal analyte in that region results in low-end sensitivity problems.

Perhaps the most common and most sensitive method of assay heretofore in use involves covalently immobilizing a capture agent (e.g. monoclonal antibody) a solid support, such as a microtiter well, a cup or a tube. Such coated cup assays are well-known in the art. They have been used since the 1960's with radioimmunoassays, and remain common in many of the clinical analyzers in laboratories today, such as the Amerlite, Cyber-fluor, Delfia, and the ES-300 systems. See also U.S. Pat. No. 4,376,110. Advantages of coated cup assays include that they provide a homogeneous and single layer of analyte for analysis. Although coated cup technology is currently used in various immunoassay formats, the time required for the assay components to diffuse to the coated wall is excessive. Heating and constant shaking can reduce incubation times, but sensitive assays such as TSH and CEA still require 30–60 minutes for the incubation of analyte, signal producing agent and immobilized capture antibody. Additionally, the assay is highly dependent on the manufacture of cups with an evenly distributed coating of capture antibody on the cup surface.

Another type of immunoassay involves attachment of the capture antibody to a mobile solid phase, such as latex or other polymeric microbeads, some of which are magnetically responsive. Centrifugation, settling, filtration, or magnetic means are used to accomplish the bound/free separation. See U.S. Pat. Nos. 5,242,837; 5,169,754; 4,988,618; 5,206,159; 4,343,901; and 4,267,235. In certain cases, the act of binding to the particle, introduces a change in a property of the particle, which can be detected. While the benefits of a mobile solid phase include increased surface area and therefore decreased incubation times, problems with these assays include clogging of tubing, aggregation, settling, and in the cases where centrifugation is used, extremely complicated automation procedures. Most of the magnetic particles are large (1000–5000 nm in diameter,) so the problems of clogging and settling are particularly prevalent, and must be engineered around.

Recently, a class of magnetic materials appropriately referred to as ferrofluids have been introduced into immunoassay technology. Ferrofluids are nanosized crystals or crystal clusters of magnetite which are coated with materials that act as surfactants. Historically, most surfactants were, indeed, detergents; more recently, polymers or proteins have been used in that role. Ferrofluids have a variety of unique properties, among which is that thermodynamically they act as solutes. Like lyophilic colloids, they interact strongly with solvent and exhibit a variety of most unusual phenomena. With the availability of polymer/protein coated ferrofluids and the use of appropriate coupling chemistries, immunoassays in which ferrofluids have been used to perform bound/free separations have been devised. See U.S. Pat. Nos. 4,795,698; 4,965,007; 5,283,079; and 5,238,811. Ferrofluids have a decided advantage when compared to other capture systems, particularly those that employ relatively large magnetic particles (greater than 0.5 microns), which is attributable to translational and rotational diffusion. Thus, by employing ferrofluids in immunoassays, binding reactions proceed at diffusion controlled rates and do not require the constant mixing necessary when larger particles are used.

For polymer/protein coated ferrofluids wherein the crystal core is composed of magnetite clusters, the magnetic gradient required to effect separation is inversely related to the numbers of crystals in the clusters. Typically, crystal sizes are in the range of about 4–12 nm, while after coupling of bioligand, sizes range from about 20 nm to as large as 300–400 nm. Materials synthesized from crystal clusters up to about 120 nm that are well coated with polymer/protein will exhibit colloidal stability for long periods (such materials typically show no signs of settling for up to one month, or longer). As the size decreases within the optimal range for this bioligand-coupled material, which is 60 to 150 nm, such materials become more difficult to separate magnetically. Materials in the 20 nm range are difficult to effectively separate, even in high gradient magnetic separation devices employing very fine stainless steel wires capable of generating gradients of 150–200 kGauss/cm. Materials of 40–60 nm, which appear to be composed of cores having a cluster of three to six magnetite crystals, can be effectively collected with such gradients.

The above class of materials are particularly useful in performing bioanalytical separations, due principally to the ability of such materials to diffuse and to be magnetically immobilized. Since diffusion constants are inversely related to colloid size, the smaller bioligand-coupled ferrofluids have notable advantage over larger size materials. Further, in that smaller diameter materials have greater surface area per unit mass, such materials provide additional advantages over larger size materials when used in binding reactions. For example, less material is required to be introduced into the system; i.e., the binding particles represent a smaller volume fraction. As documented in commonly owned U.S. Pat. No. 5,466,574, due to their surface-to-mass ratio, the quantities of these ferrofluid particles can be manipulated, so as to be deposited on a collection surface in a substantially uniform thickness, which may aptly be characterized as a monolayer. This property makes possible quantitative signal detection while the magnetic particles are immobilized on wires, microtiter cups, rods, sheets, or other solid supports. However, the experience gained with forming such monolayers in external collection devices of the type described in U.S. patent application Ser. No. 08/006,071, has shown that while monolayers can be regularly and reproducibly formed in the apparatus disclosed in that application, as well as related U.S. Pat. No. 5,186,827 and commonly owned U.S. patent application Ser. No. 08/424,271, these monolayers are not sufficiently stable to withstand repeated and vigorous washing without constructing wash devices which are highly controlled, insofar as the rate of addition of wash solution and shearing force of solution removal are concerned. When too vigorously washed, the shearing force of the meniscus as it travels past the monolayer distorts the monolayer such that multilayering occurs at the bottom of the cup. Additionally, prolonged exposure of the monolayer to a high gradient magnetic field which is not radially symmetrical will result in lateral movement of the particles on the collection surface resulting in clumping in the region of highest field gradient. This can occur in radial fields where relatively small inhomogeneities exist. Thus, any inhomogeneities will result in undesired clumping and resultant distortion of the monolayer. In automated magnetic separation devices in which space is limited, the constraints imposed often detract from the ability of the device to produce highly symmetrical gradients. Consequently, the accumulation of particles in a clump precludes the possibility of reading signal generated by the labeled specific receptor while the analyte is magnetically immobilized on the cup wall. Such particle clumping also causes unbound signal to be trapped, which can result in higher background signal. Resuspension is, therefore, required in the washing and signal detection stages, which is undesirable for many reasons, including, above all, that resuspension is an extra step requiring time and manipulation, which to be reproducible on an automated machine would require considerable additional engineering and programming.

SUMMARY OF THE INVENTION

The present invention provides a way of ensuring the non-reorientation of magnetically collected material, e.g., during the processing steps of an assay method which may include removal of the collection surface from the magnetic field, washing of the collected material, reagent addition, buffer or solvent changes, sequential reactions, heating, drying, irradiation, and sonication. Non-reorientation is achieved by linkage of the magnetic particle to the collection surface via a specific binding pair. The reaction of the specific binding pair may be either simultaneous with or prior to magnetic particle collection. Optionally, the specific binding pair reaction is reversible. The present invention may also be practiced so as to facilitate the formation of a monolayer of analyte-bearing magnetic microparticles upon collection.

The instant invention also provides an immunoassay which combines operational elements of a coated cup assay with operational elements of a magnetic bead or ferrofluid assay. By providing a collection surface upon which is coated one member of a specific binding pair, the other member of which pair is borne by the magnetic material, a substantially uniform thickness or layer of magnetic particles, and thus, analyte can be obtained. This layer of particles and analyte in the immobilized state can then be maintained in place throughout the rigors of reagent addition and repeated washings without appreciable displacement or redistribution. Thus, the assay of this invention offers the speed of a diffusion-controlled kinetics, as in a ferrofluid assay, the speed of collection of labeled target substance, as in a magnetic assay, as well as the ability to magnetically monolayer ferrofluid in the manner described in commonly owed U.S. Pat. No. 5,466,574, all of which is combined with the ease of washing and signal detection found in a coated cup assay.

In one embodiment, the method of the present invention is applied to the determination of the presence or quantity of an analyte having at least one characteristic determinant, in a test sample. Such an assay is carried out by adding to the test sample a signal producing agent comprising a binding substance that binds specifically to a characteristic determinant of the analyte and a capture agent comprising a specific binding substance which binds specifically to the other binding site of the analyte and which is directly bonded to magnetic particles or adapted to be bonded to magnetic particles provided in the test sample, the magnetic particles bearing one member of a specific binding pair for collection. The test sample is then subjected to conditions causing complex formation between the analyte, the signal producing agent and the capture agent. The test sample is then contacted with a collection surface on which is affixed the other member of the specific binding pair for collection, and subjected to the influence of a magnetic field to promote binding interactions between the specific binding members and cause the complex-bound magnetic particles to collect on the collection surface. The uncomplexed signal producing agent is thereafter separated from the complexed signal producing agent, and signal is detected in the separated, complexed signal producing agent, or optionally from the separated uncomplexed original producing agent, from which the presence or quantity of analyte in the test sample can be determined. The magnetic particles are typically present in an amount in excess of that required to bind all of the formed complexes.

According to its broader aspects, the present invention affords an improvement in analytical methods involving collection of analyte-bearing magnetic particles from a test sample on a collection surface associated with a receptacle, wherein a treatment solution is deposited in the receptacle in an amount sufficient to submerge the collected analyte-bearing magnetic particles and the treatment solution is evacuated from the receptacle, but without appreciable displacement caused by the addition or removal of the treatment solution. The improvement lies in directly or indirectly bonding to the magnetic particles one member of a specific binding pair, directly or indirectly affixing to the collection surface the other member of the specific binding pair and contacting the collection surface with the test sample under the influence of a magnetic field to promote binding interaction between the specific binding pair members and cause binding of the analyte-bearing magnetic particles to the collection surface, whereby the analyte-bearing magnetic particles are maintained in place on the collection surface. In this way, the analyte-bearing magnetic particles are maintained in place on the collection surface, without appreciable displacement or reorientation caused by addition or removal of the treatment solution. Representative examples of treatment solutions used in this method are signal producing agents, wash solutions, physiological buffers, biological fluids, such as serum or plasma, various formulations of tissue culture media, such as DMEM, RPMI, Hams f12, distilled water, or any other substance or solutions that may be required in conducting the assays described herein.

In a further embodiment of the present invention, the presence or quantity of analyte of the type previously described is determined in a two stage assay. The first stage of the assay comprises the steps of mixing together the test sample and a capture agent which contains one member of a first specific binding pair for capture, and a binding substance that binds selectively to one of the first or second binding sites on the analyte. The test sample containing the capture agent is then exposed to conditions allowing complex formation to occur between the analyte and capture agent. Formed complexes (capture agent and analyte) are contacted with an excess of magnetic particles bearing the other member of the first specific binding pair, and one member of a second specific binding pair for collection, under conditions causing binding of the members of the first specific binding pair. The test sample is then placed into a receptacle containing a collection surface to which is affixed the other member of the second specific binding pair, under the influence of a magnetic field to promote binding interaction between complex-bound, magnetic particles and the other member of the second specific binding pair, causing the complex-bound magnetic particles to be collected on the collection surface. Complex bound magnetic particles are separated from the test sample, e.g. via washing with a wash solution or simple aspiration. The second stage of the assay comprises the steps of contacting the complex-bound magnetic particles with a signal producing agent comprising a specific binding substance that binds specifically to the other of the binding sites on the analyte under conditions causing binding of the signal producing agent to analyte contained in the complex-bound magnetic particles. The unbound signal producing agent is then separated from complex-bound signal producing agent, e.g. by washing or aspiration. Signal is then detected from the bound signal producing agent, from which the presence and/or quantity of said analyte in said test sample is determined.

In yet another embodiment of the present invention the presence or quantity of analyte in a test fluid is determined by means of a "phasing" phenomenon. In this embodiment the assay is again carried out in two stages, the first stage being substantially as described immediately above. The second stage of this method comprises the steps of placing the separated complex-bound magnetic particles in a non-magnetic fluid phase and then contacting the complex-bound magnetic particles on the collection surface with a solution containing a non-magnetic signal producing agent, which comprises a specific binding substance that binds specifically to the other binding site on the analyte, and a quantity of colloidal magnetic particles. The added solution forms a distinct phase in the non-magnetic fluid phase, with the magnetic and non-magnetic components of the solution being stably confined within the distinct phase. A magnetic field is imposed in the vicinity of the collection surface, having a region of sufficiently high intensity to cause the distinct phase to be positioned adjacent to the collection surface. The specific binding substance of the signal producing agent then binds the analyte present in the complex-bound magnetic particles. Unbound signal producing agent is separated from analyte bound signal producing agent and the presence and/or quantity of the analyte in the test sample is determined.

DETAILED DESCRIPTION OF THE PREFERRED EMBODIMENTS

According to a preferred embodiment, the present invention provides an assay method having the distinctive capability of immobilizing and preventing the reorientation or lateral movement of magnetic microparticles after magnetic collection of such particles upon a collection surface. This capability is highly advantageous in many analytical applications. The immobilization is achieved with the coating of one member of a specific binding pair to the collection surface. The other member of the specific binding pair is borne by the magnetic microparticle. In the process of magnetic collection of the magnetic microparticle, the binding pairs react to form a stable bond, optionally covalent. This bond must be strong enough to withstand whatever forces will be operative upon the collection surface and the immobilized microparticles. Depending on the requirements of the system, these forces may include removal of the collection surface from the magnetic field, washing of the microparticles, reagent addition, buffer or solvent changes, sequential reactions, heating, drying, irradiation, and sonication.

The terms "analyte" or "target substance" as used herein, refer to a wide variety of substances of biological or medical interest which are measurable individually or as a group. Examples include hormones, proteins, peptides, oligonucleotides, drugs, chemical substances, macromolecules (e.g., nucleic acids-RNA, DNA) and particulate analytes, which include bioparticles such as cells, viruses, bacteria and the like. The term "determinant," when used in reference to any of the foregoing analytes or target substances, means that portion of the target surface involved in and responsible for selective binding to the specific binding substance, the presence of which is required for selective binding to occur. In fundamental terms, determinants are the molecular contact regions on analytes or target substances that are recognized by receptors in specific binding pair reactions. The term "specific binding pair" as used herein includes antigen-antibody, receptor-hormone, receptor-ligand, agonist-antagonist, lectin-carbohydrate, nucleic acid (RNA or DNA) hybridizing sequences, Fc receptor of mouse IgG-protein A, avidin-biotin, streptavidin-biotin and virus-receptor pairs. Various other determinant-specific binding substance combinations are determinable using the methods of this invention, as will be apparent to those skilled in the art. The term "antibody" as used herein includes immunoglobulins, monoclonal or polyclonal antibodies, immunoreactive immunoglobulin fragments, single chain antibodies, and peptides, oligonucleotides or a combination thereof which specifically recognize determinants with specificity similar to traditionally generated antibodies. The term "monolayer" as used herein describes a relatively thin layer of analyte or target substance-bound magnetic particles collected in substantially uniform thickness, such that essentially no interfering substances may be entrapped within the layer.

The preferred magnetic particles for use in carrying out this invention are particles that behave as colloids. Such particles are characterized by their sub-micron particle size, which is generally less than about 200 nanometers (nm) (0.20 microns), and their stability to gravitational separation from solution for extended periods of time. Suitable materials are composed of a crystalline core of superparamagnetic material surrounded by molecules which are bonded, e.g. physically absorbed or covalently attached, to the magnetic core and which confer stabilizing colloidal properties. The size of the colloidal particles is sufficiently small that they do not contain a complete magnetic domain, and their Brownian energy exceeds their magnetic moment. As a consequence, North Pole, South Pole alignment and subsequent mutual attraction/repulsion of these colloidal magnetic particles does not appear to occur even in moderately strong magnetic fields, contributing to their solution stability. Accordingly, colloidal magnetic particles are not readily separable from solution as such even with powerful electromagnets, but instead require a magnetic gradient to be generated within the test medium in which the particles are suspended in order to achieve separation of the discrete particles.

Magnetic particles having the above-described properties can be prepared as described in U.S. Pat. No. 4,795,698, and commonly owned U.S. application Ser. Nos. 397,106, and 08/482,448.

With the proper collection vessels and magnetic fields, the colloidal magnetic particle or ferrofluids described above can be manipulated to form a relatively thin, substantially uniform layer of particles such that no interfering substances may be entrapped within such layer. These thin layers are believed to be monolayers of magnetic material bearing target substance which is bound to the magnetic material. The manner in which the methods of the present invention facilitate such monolayer formation constitutes a notable improvement over existing magnetic immunoassays and coated cup-type assays. Since the specific binding reaction can probably not occur if the collected particles are layered one on top of the other, due to impeded contact between the two members of the specific binding pair, any layer of magnetic particles substantially in excess of a monolayer would not be immobilized on the collection surface. However, upon change in the magnetic field, washing, reagent addition or any other disturbance of the environment of the collection surface, the collected multiple layers of magnetic particles may be dislodged from their collection site. These particles may then migrate to a new location on the collection surface not occupied by magnetic particles, and the binding pair member borne by such particles could then react with the binding pair member affixed to the collection surface at the new location.

In some situations, it may be desirable to obtain a monolayer of magnetic particle-bound target substance, but other constraints may not allow for realization of the specialized conditions required to form such layers. The present invention can be supplemented so as to initially form multilayers of magnetic particles, perhaps with a magnetic field that is not optimal for the formation of monolayers or with excessive magnetic material collected upon a surface, i.e. magnetic particle excess. One such embodiment involves collection with a monopole. The bottom-most layer of magnetic particles would form an immobilized monolayer via the specific binding pair reaction, but the upper layers would not. Repositioning the collection vessel, such that a new portion of the vessel wall is exposed to the region of highest magnetic field will result in a newly exposed "collection surface." The upper layers of the magnetic particles would cascade over to the newly exposed collection surface, where immobilization would occur. This procedure could be repeated until all of the magnetic particles have been immobilized in a monolayer. Alternately, excess magnetic particles could be added to a system, followed by binding pair reaction and immobilization of the analyte-bearing magnetic particles on the collection surface with unbound components discarded, typically by removal from the magnetic field. It will be appreciated that by limiting the area of the collection surface on which the specific binding pair member is affixed, a pre-determined quantity of magnetic material or target substance can be immobilized. This capability may be beneficially used in the collection of some fixed number of mammalian cells in a monolayer on a microscope slide for further analysis. As a practical example, this aspect of the present invention should enable the critical examination of 100,000 CD4+ cells. Magnetically bound cells would be magnetically immobilized upon a collection surface, the binding pair reaction would take place, and excess cells removed in the absence of a magnetic field.

An example of an assay embodying the method of this invention is a sandwich assay employing two monoclonal antibodies directed towards different regions of an analyte of clinical significance, such as human chorionic gonadotropin (hCG) or thyroid stimulating hormone (TSH.) One antibody may be labeled with a signal generating enzyme such as horseradish peroxidase (HRP) or alkaline phosphatase (AP), and the other antibody could be conjugated with biotin or a hapten which can be immunologically recognized without difficulty, to facilitate analyte capture. A magnetic ferrofluid particle could be coated with avidin, streptavidin, or anti-hapten, as the case may be, and optionally coated with two such types of materials. The assay could be performed in a microtiter cup or other similar receptacle, which had been coated with either the same specific binding pair member to which the second monoclonal antibody is conjugated, or a member of some other specific binding pair which is bound either directly, or indirectly, e.g. via a protein or other polymer coating, to the collection surface. The assay could proceed by the formation of the sandwiches resulting from incubation of the monoclonal antibodies with the sample in the coated cup. This first incubation might take 2–10 minutes. A subsequent addition of coated ferrofluid would require 2–10 minutes. Magnetic collection of the analyte-bound ferrofluid using the appropriate magnetic design would remove all ferrofluid and all labeled analyte from solution. Preferably, the magnetic array would be designed such that the magnetic material would be attracted to the collection surface evenly, such that a layer of substantially uniform thickness would be formed. Optionally, by controlling the amount of ferrofluid in the assay as described in commonly owned U.S. Pat. No. 5,466,574, a substantially thin layer or a monolayer could be obtained. Magnetic collection might require 30 seconds-5 minutes. Excess signal producing antibody and unbound sample would be washed out using a compatible wash buffer, but the magnetically collected material would remain as uniformly deposited on the collection surface because it is bound to said surface via the specific binding pair reaction. After the addition of enzyme substrate, the signal could be detected, optionally with the collection surface remaining in the magnetic field.

The results obtained from assays conducted as generally described above, and more specifically in the examples that follow, are significantly better than either coated cup assays or magnetic ferrofluid assays. The improvement over coated cup assays is realized in the significantly shorter time needed for incubations. For example, in a coated cup assay, if a biotinylated capture antibody is used with a streptavidin- or avidin-coated cup, at least two kinds of reactions occur. Capture antibody can react with the cup first, with the sandwich reaction taking place thereafter. Alternatively, sandwich can form in solution and diffuse to the wall to initiate the capture reaction. Such reactions require considerable time. On the other hand, if a sandwich is allowed to form in solution and ferrofluid is subsequently added to the system so as to capture the sandwiches, and this step is followed by magnetic separation, the kinetics of the latter procedure are significantly quicker.

The improvement over magnetic assays is realized in the enhanced (higher) signal at the "high end" and the increased signal-to-noise ratio at the "low end." The ability to avoid resuspension of the magnetic material in connection with washing or signal detection operations also results in easier automation and less restrictive magnetic arrays. The improvement over previous monolaying techniques, such as described in U.S. Pat. No. 5,466,574 is realized in that simpler wash schemes can be employed, as even vigorous washing will not distort or displace the monolayer.

Furthermore, material so collected can be removed from the magnetic field and still exist as a monolayer for washing or signal detection. Finally, improved washing can decrease background signal, increasing signal-to-noise ratios and reproducibility.

Of course the methods of the present invention can also be utilized in performing assays other than the sandwich assay described above. The present invention is also applicable in competitive assays in which there is commonly only one characteristic determinant on the target substance, as well as dual stage assays for more complex molecules. Some of the dual stage assays are used to differentiate acute infection from chronic infection by determining the presence of patient IgM or IgG specific antibodies, respectively.

The use of the present invention in dual stage assays provides particular benefits not previously obtainable. In a dual stage assay, a mixture of substances is removed from solution in the first stage with a specific binding substance. This mixture is further subdivided by the second stage incubation with a different specific binding substance, which also comprises a detectable label. The ease of washing afforded by the methods of the present invention is important in a dual stage assay. However, the second incubation is constrained by the immobilization of the analyte of interest on the collection surface. However, inasmuch as the first stage was a magnetic assay, the second stage can be accelerated by using the same magnetic fields. For example, the non-magnetic, labeled, specific binding substance used in the second stage could be provided in a solution which also contains a quantity of small magnetic particles capable of forming ferrophases, as described in commonly owned U.S. application Ser. No. 08/228,818. If this magnetic ferrophase were added to a non-magnetic liquid phase in the collection chamber, the ferrophasing phenomenon could be utilized to transport both the magnetic and the non-magnetic components of the newly added solution to a region of the collection vessel very close to the collection surface. Since the specific binding material would be so close to the immobilized substances, the reaction would proceed at a rate significantly faster than the reaction rate of an immobilized substance with a second substance in solution. The small magnetic particles which are collected during the second incubation can be easily washed away upon removal of the collection surface from the influence of the magnetic field, as they have no affinity for the collection surface. Alternatively, by choosing a very small or weakly magnetic ferrofluid to create the ferrophase none of it would collect given the magnetic field gradient strength normally employed for separating the ferrofluid previously collected and immobilized.

An alternative method for a dual stage assay is also provided when the instant invention is combined with the teaching of commonly owned U.S. application Ser. No. 08/395,967. In this embodiment of the invention, the specific binding pair that immobilizes the magnetic particle on the collection surface forms a dissociable bond. For example, the binding pair could comprise a poly-A tail coating on the magnetic particle and a poly-T tail affixed to the collection surface. Removal from the magnetic field, combined with a slight increase in temperature would dissociate the bond between this specific binding pair, thereby releasing the magnetic material from the collection surface. Therefore, the second stage of the dual stage reaction with the labeled, specific binding substance could proceed in solution, limited only by diffusion-controlled kinetics, which are significantly faster than the kinetics of a reaction with an immobilized substance. After completion of the second stage reaction magnetic collection would separate the complexed magnetic material from the non-magnetic, uncomplexed material and then the temperature would be lowered and re-immobilization would occur via hybridization. The uncomplexed material would be washed away with a compatible buffer, and the detection of the labeled substance could proceed.

It will be appreciated by those skilled in the art that the range of applications of the instant invention is not limited to the examples provided herein. The specific binding pairs listed above could include an extensive list of haptens, antigen/antibody pairs, or other specific binding pairs. The present invention provides for both the use of one binding pair in two different situations, but could also include two totally different binding pairs, or a single binding pair, using two different analogs of a substance. For example, a magnetic particle coated solely with avidin could be used, while the coating on the collection surface and the capture agent could comprise biotin. In the second case, if two binding pairs were to be used, poly-A/poly-T could be used to coat the collection surface and the magnetic particle, respectively. The same magnetic particle could also have a streptavidin coating as a specific binding pair member for capture, to bind a biotinylated capture monoclonal antibody. It is also possible that the two binding pairs could share a common member. For example, the magnetic particle could be coated solely with streptavidin, but the capture monoclonal antibody could be biotinylated and the collection surface could be coated with anti-streptavidin. In the third case, the coating on the magnetic particle could comprise solely streptavidin, but the capture monoclonal antibody could be biotinylated and the collection surface could have iminobiotin affixed thereon. It will be understood by those skilled in the art that the specific binding pairs may be provided differently, even if they comprise the same substance. For example, the capture antibody could be biotinylated, but the biotin on the collection surface need not be provided on an antibody, or even a protein. Coating a synthetic polymer with biotin may prove more advantageous, depending on the desired application.

It may also be advantageous in certain applications to separate the magnetic collection from the binding pair reaction. This variation is also within the scope of the present invention. For example, it may be advantageous to use a magnetic particle which has been coated with the specific receptor for the analyte or target substance. It is also possible that in such situations long incubations are required, such that the competing reaction of the binding pair member on the magnetic particle with the binding pair member on the collection surface proceeds to a substantial extent and therefore the main reaction for the capture of the target substance would be impaired. To be able to use magnetic particles directly coated with antibody, for example, which may be useful for other reasons, the binding pair reaction could be engineered to occur either immediately before or after magnetic separation. One example of such a reaction can be envisioned where the specific binding pair reaction requires the addition of a reagent to occur. For example, the collection surface and the magnetic particle might both be coated with biotin. Immediately after the magnetic separation, streptavidin or avidin could be added to immobilize the magnetic particle by linking the particle to the collection surface. Another example might be to have a first hapten coated on the magnetic particle and a second hapten coated upon the collection surface. A bifunctional antibody with specificity to the two haptens could be added either immediately before or just after magnetic separation and would immobilize the magnetic particles on the collection surface. An alternative approach would be to a use a binding pair which requires a co-factor or certain solution conditions to become active. For example, calcium-dependent antibody-determinant reactions could be employed for this purpose. (See *Protein-Metal Interactions*, Chapter 9.) One of the reactants could be used to coat the collection surface or the magnetic particle. After the reaction with the target substance has occurred, calcium could be added to the test sample, which could be placed in the magnetic field and the magnetic collection could occur. Also, manipulation of pH, temperature, ionic strength, or other conditions may be employed to change the conformation of a member of the specific binding pair. Yet another approach is to use temperature control, e.g. to regulate the binding of DNA or RNA probes. For example, two nucleic acid probes could be borne upon the magnetic particle. One probe would be complementary to the target substance, and one complementary to a probe affixed to the collection surface. These probes would be of sufficiently different length, that the so-called "melting temperature" ($T_m$) of the two hybridization partners is significantly different. Preferably, the target substance probe would be longer and therefore have a higher $T_m$. Therefore, the initial incubation with the target substance could be conducted at a temperature that would allow the annealing of the probe borne upon the magnetic particle with the target nucleic acid. However, this temperature would be too high to allow the annealing of the probe to the collection surface to occur. This second annealing reaction would only be allowed to occur after the temperature had been reduced, optionally after the solution had been exposed to a magnetic field gradient for collection.

Although the present invention is described herein primarily with reference to immunoassay applications, the invention is not limited to immunoassay. Nucleic acid separation and detection are also within the scope of this invention. Thus the methods described herein may be used in sample preparation for polymerase chain reaction (PCR) or other applications involving recognition and separation of a unique segment of nucleic acid with a low copy number. For example, a mixture of DNA, which contains only a few DNA molecules of interest could be selected from solution by means of a biotinylated probe complementary to a unique segment of nucleic acid of interest. Collection and immobilization in accordance with the present invention would allow for vigorous washing, which would enable the removal of all contaminating nucleic acid from the collection surface. The resultant DNA could be released from the collection surface as described hereinabove, or as described in commonly owned U.S. application Ser. No. 08/395,967 for use in PCR or other target amplification systems. Alternately, the DNA could be detected while immobilized on the collection surface by the use of a second probe which may be enzymatically labeled, or have some other detectable characteristic.

Various signal producing substances may be used for generating a detectable signal. These include substances selected from the group consisting of molecules or ions directly or indirectly detectable based on light absorbance, fluorescence, phosphorescence, or luminescence (e.g. chemiluminescence or electrochemiluminescence) properties; molecules or ions detectable by their radioactive property; and molecules or ions detectable by their nuclear magnetic resonance or paramagnetic properties.

A wide range of fluorophores, enzymes, or various molecules that can be made to emit light upon excitation could be used to produce the signals, all of which are well known in the art.

The collection surface for the assays and other methods described herein may include microtiter cups, coated tubes, microtiter plates, capillary vessels, microscope slides, or other small or large chambers.

The methods described herein lend themselves nicely to microfabricated chips or biosensors, since the present invention provides for the construction of arrays of captured molecules, cells, or combinations thereof, the size of which is limited only by engineering constraints.

The following examples will serve to illustrate the principles of this invention; however, these examples should not be construed as limiting the scope of this invention.

EXAMPLE 1

Increase in Signal in a Monolayered Nanoparticle Assay

A sandwich type immunoassay was used for all of the following examples set forth herein except where otherwise noted. Briefly, the capture monoclonal antibody was biotinylated, the signal monoclonal antibody was conjugated to peroxidase enzyme, the analyte was thyroid stimulating hormone (TSH) and the ferrofluid was prepared as described in commonly owned U.S. application Ser. No. 08/482,448 and covalently coupled to streptavidin.

The assay method of this invention affords advantages over conventional immunomagnetic assays in which the test receptacle is not coated with a "collection" antibody, as illustrated by the following experiment comparing the two methods.

Coated cups were prepared by coating with BSA, biotinylated by the following procedure. Bovine serum albumin (BSA) was obtained from Intergen (Purchase, N.Y.) and biotinylated with an excess of biotin ester (succinimidyl 6-(biotinamido)hexanoate from Molecular Probes (Eugene, Oreg.) After quenching, the biotinylated BSA was purified over a Sephadex G25 column. To coat the cups, 200 μl of biotin-BSA at 1 mg/ml in 50 mM bicarbonate buffer pH 8.5 was added to polystyrene cups and incubated at 4° C. overnight. After overnight incubation, each cup was washed with 300 μl of wash buffer (20 mM ionic strength buffer pH 8.5, containing 0.05% non-ionic detergent) to remove unbound biotin-BSA. Washing was repeated four more times. After final wash, all the wash buffer was removed and the cups were stored at 4° C. until use.

The assay was performed in cups coated as described above by incubating 80 μl of TSH serum standard with 40 μl of monoclonal antibody (MoAb) mixture (biotinylated capture MoAb at 1.75 μg/ml and MoAb-peroxidase at 0.75 μg/ml) in 0.1M ionic strength buffer, pH 7.5 containing 5% BSA in a cup at 37° C. for 10 minutes to form capture MoAb-TSH-MoAb-peroxidase sandwiches. Then 40 μl of streptavidin ferrofluid (S.Av. F.F.) at 0.0125 mg/ml in ferrofluid dilution buffer (Immunicon Corp., Huntingdon Valley, Pa.) was added to the above reaction mixture and incubated for another 3 minutes to bind all capture MoAb-biotin. The cups were then transferred to a quadrupole magnetic nest as described in U.S. Pat. No. 5,186,827, the entire disclosure of which is incorporated by reference herein, to separate ferrofluid from unreacted MoAb-peroxidase. After 2 minutes of separation, the supernatant was removed and 300 μl of wash buffer (20 mM ionic strength buffer, pH 8.5 containing 0.05% non-ionic detergent) was added to the cups. This washing procedure was repeated three more times.

The experiment was duplicated in uncoated cups with resuspension of the ferrofluid. After the final wash step, all the supernatant was removed, the cups were removed from the magnetic nest and 200 μl of chemiluminescence signal reagent containing luminol was added. The ferrofluid was resuspended by mixing signal reagent with a pipet many times and the signal was read 5 minutes after the addition of the signal reagent using a chemiluminescence plate reader.

The procedure used on the cups coated with biotinylated BSA using immobilized ferrofluid, was as follows. After the final wash step, all the supernatant was removed and 200 μl of chemiluminescence signal reagent was added to the cup in the magnetic nest. The signal was read 5 minutes after signal reagent addition using a chemiluminescence plate reader with the ferrofluid immobilized on the cup in the magnetic nest. The data for these tests are compiled in table I below.

TABLE I

| TSH STD (μIU/ml) | Signal from resuspended ferrofluid | Signal from ferrofluid immobilized on the cup |
|---|---|---|
| 0.0 | 3.0 | 2.7 |
| 0.13 | 11.9 | 16.7 |
| 0.75 | 127 | 162.5 |
| 4.0 | 900.5 | 991 |
| 20 | 4053 | 4505 |
| 110 | 16433 | 17644 | all signal values are in CHL units

Note that at the low end, the signal-to-noise ratio has dramatically improved with the ferrofluid immobilized. The signal-to-noise ratio improved from 11.9:3.0 (or 4.0) to 16.7:2.7 (or 6.2). At the high end, the total signal has increased approximately 7% as well.

EXAMPLE 2

Signal Due to Ferrofluid Particles Reacting with the Coated Cup Without Magnetic Collection The amount of signal generated by magnetic particles reacting with the coated cup in the absence of magnetic separation was experimentally determined, so as to assess the advantages magnetics bring to this system. In carrying out this experiment, 80 μl of TSH serum standard (110 μIU/ml) was incubated with 40 μl of monoclonal antibody mixture as described in example 1, above, in a biotin-coated cup at 37° C. for 10 minutes to form capture MoAb-TSH-MoAb-peroxidase sandwiches. Then 40 μl of S.Av.F.F. in ferrofluid dilution buffer (Immunicon Corp., Huntingdon Valley, Pa.) was added to the resulting mixture and incubated for another 8 minutes to bind all capture MoAb-biotin. After ferrofluid incubation, but without magnetic separation, the supernatant was removed and 300 μl of wash buffer (20 mM ionic strength buffer pH 8.5 containing non-ionic detergent) was added to the cup. This was repeated three more times. Then 200 μl of signal reagent was added to the cup and chemiluminescence signal was read at 5 minutes using a chemiluminescence plate reader.

Table II shows the signal obtained from coated cups without magnetic collection. For comparison, the signal with magnetic collection in coated cups is also shown. The signal obtained by performing magnetic collection was used as 100%.

TABLE II

| | Signal | % signal |
|---|---|---|
| Coated cup without magnetic collection | 680 | 4.5% |
| Coated cup with magnetic collection | 15097 | 100% |

Note that less than 5% of the signal is obtained if a magnetic collection is not done. Although this signal could be increased without magnetic collection by increasing the incubation time, to obtain a full signal, an extremely long assay would be required. These data clearly demonstrate the advantage of combining a liquid stage ferrofluid assay, coated well methodology and magnetically assisted collection.

EXAMPLE 3

Signal Improvement Not Due to Protein Coating or Non-Specific Interactions

The improvement in signal readout is due to the creation of a stable monolayer as illustrated in the following example. A comparison experiment was performed as described in example 1, above, using uncoated cups, cups coated with biotinylated BSA and BSA only. In the case of BSA only, two effects can be anticipated. These are that the monolayer can be distorted such that signal will be lost via quenching in multilayered ferrofluid, or ferrofluid could be lost during the wash steps. Therefore, the assay of example 1 was repeated with cups treated as described above, some with resuspension of the magnetic material. The incubation times were 10 minutes for the antibody incubation, 5 minutes for the streptavidin ferrofluid incubation, and 3 minutes for the magnetic collection. The analyte concentration was 110 μIU/ml. The results are tabulated in Table III below. Signal from resuspended ferrofluid in an uncoated cup is set as 100%

TABLE III

| | Signal | % signal |
|---|---|---|
| Ferrofluid resuspended into solution in an uncoated cup | 16732 | 100% |
| Ferrofluid not resuspended in an uncoated cup | 13881 | 83% |
| Ferrofluid not resuspended in BSA coated cup | 13718 | 82% |
| Ferrofluid not resuspended in biotin-BSA coated cup | 18077 | 108% |

Note that not resuspending the ferrofluid in an uncoated cup results in the loss of about 17% of the signal. In this case, the monolayer has been destroyed by the repeated washings and reagent addition, and a multilayer of magnetic material has reduced the available signal. Coating the cup with BSA has no appreciable effect on this result. However, not resuspending the magnetic material in a cup which has been coated with one member of a specific binding pair, with the other member borne upon the magnetic material, results in higher signal than the control. It this case, effective washing and monolayered analyte combine to increase the signal available for analysis.

EXAMPLE 4

Direct Conjugated Ferrofluid Shows Higher Signal Generation in the Resuspended State Than in the Multilayered State To demonstrate that a monolayer phenomenon induced by specific interaction between ferrofluid and cup is required even if ferrofluid having capture antibody directly bonded thereto is employed, the following experiments were done. A monoclonal antibody (anti-TSH) with no affinity for biotin was directly coupled to ferrofluid. It was prepared by the following procedure: BSA ferrofluid was prepared as described in commonly owned U.S. patent application Ser. No. 08/482,448. The BSA ferrofluid was activated using N-succinimidyl-4-(N-maleimido methyl)cyclohexane-1-carboxylate (SMCC) (Pierce, Rockford, Ill.) TSH capture monoclonal antibody was activated with Traut's reagent (Pierce, Rockford, Ill.) and purified over a PD-10 column (Pharmacia Biotech, Uppsala, Sweden.) The activated ferrofluid was mixed with the activated monoclonal antibody and allowed to react at room temperature for 1 hour followed by overnight reaction at 4° C. After quenching, the ferrofluid was washed and a final 0.2 micron filtration was performed.

For the experiment, 80 µl of TSH serum standard (110 µIU/ml) was incubated with 40 µl of MoAb-peroxidase (0.75 µg/ml) in 0.1M ionic strength buffer pH 7.5 containing 5% BSA and 40 µl of anti-TSH capture MoAb coupled-ferrofluid at 0.018 mg/ml in ferrofluid dilution buffer (Immunicon Corp., Huntingdon Valley, Pa.) in a microtiter cup at 377° C. for 15 minutes to form ferrofluid-TSH-MoAb-peroxidase sandwiches. The cup was then transferred to a quadrupole magnetic nest, as previously noted, to separate ferrofluid from unreacted MoAb-peroxidase. After 3 minutes of separation, the supernatant was removed and 300 µl of wash buffer was added to the cup. This was repeated three more times. After the final wash step, all the supernatant was removed and 200 µl of chemiluminescence signal reagent was added to the cup in the magnetic nest. In one set of experiments the magnetic material was resuspended and in the other the material remained immobilized. Then signal was read at 5 minutes using the chemiluminescence plate reader. These experiments were done in a biotin-BSA coated cup and in an uncoated cup and results are shown in Table IV.

TABLE IV

|  | Signal | % Signal |
| --- | --- | --- |
| Ferrofluid not resuspended in biotin-BSA coated cup | 17895 | 76% |
| Ferrofluid resuspended in uncoated cup | 23402 | 100% |

In this experiment, a non-specific receptor was coated onto the ferrofluid. Therefore, there was no specific interaction between the collection surface and the magnetic particle. These results clearly show that there is higher signal with an antibody coupled-ferrofluid in the resuspended state. In other words, magnetically immobilized materials result in quenching of signal compared to the resuspended material. Although the monolayered collection should improve signal, the monolayer is damaged by repeated washing, resulting in the pile up of ferrofluid during the wash and consequent signal loss.

EXAMPLE 5

Decrease in Non-Specific Signal of a Ferrofluid Specifically Bound to Cup Surface vs. Magnetically Immobilized Ferrofluid This experiment shows that when ferrofluid is collected uniformly and kept immobilized during washing, the trapping of free signal antibody was significantly decreased.

80 µl of the zero TSH serum standard (0 µIU/ml) was incubated with 40 µl of monoclonal antibody mixture in 0.1M ionic strength buffer pH 7.5 containing 5% BSA in a cup at 37° C. for 10 minutes to form capture MoAb-TSH-MoAb-peroxidase sandwiches. Then 40 µl of St.A.F.F. at 18.75 µg/ml in ferrofluid dilution buffer (Immunicon Corp., Huntingdon Valley, Pa.) was added to the above reaction mixture and incubated for another 5 minutes to bind all capture MoAb-biotin. The cup was then transferred to a quadrupole magnetic nest, as previously mentioned, to separate ferrofluid from unreacted MoAb-peroxidase. After 3 minutes of separation, the supernatant was removed and 300 µl of wash buffer (20 mM ionic strength buffer pH 8.5 containing non-ionic detergent) was added to the cup. This was repeated three more times.

After the final wash step, all the supernatant was removed and 200 µl of chemiluminescence signal reagent was added to the cup in the magnetic nest. Then signal was read at 5 minutes using the chemiluminescence plate reader. These experiments were done in biotin-BSA coated cups and in uncoated cups, and the results are shown in Table V. Six replicates were included in this experiment and the raw data as well as the averages and coefficients of variance (C.V.) are reported.

TABLE V

|  | Non specific signal | Average (C.V.) |
| --- | --- | --- |
| Ferrofluid immobilizized on a coated cup | 3.02 | 3.26 (9.0%) |
|  | 3.38 |  |
|  | 3.29 |  |
|  | 2.83 |  |
|  | 3.38 |  |
|  | 3.66 |  |
| Ferrofluid resuspended in an uncoated cup | 6.22 | 4.66 (27.8%) |
|  | 4.57 |  |
|  | 3.11 |  |
|  | 6.22 |  |
|  | 3.75 |  |
|  | 4.11 |  |

As can be seen from Table V, lower non-specific signal is consistently obtained with ferrofluid collected and washed in accordance with the present invention, compared to the material collected and washed while immobilized solely by magnetic means. This result could be explained by surface tension "scrubbing effects" acting on ferrofluid rigidly held onto a surface versus ferrofluid which could reorient as meniscus passes by. It is worthwhile noting that this invention results in decreased non-specific binding as well as increased signal output of specifically bound material when the latter is compared with resuspended ferrofluid, see Example 1. These data suggest that, in addition to creating stable monolayers, the specific binding pair reaction orients ferrofluid particles such that sandwiches are facing towards the center of the reaction vessel, thus resulting in higher levels of signal output compared with randomly oriented ferrofluids. Hence, it appears likely that, as applied to these kinds of assays, the method of the invention produces increased signal-to-noise ratios by two independent mechanisms.

The disclosures of each of the aforementioned, commonly owned U.S. patent applications are incorporated by reference in the present specification, as set forth herein in full.

While various aspects of the present invention have been described and exemplified above in terms of certain preferred embodiments, various other embodiments will be apparent to those skilled in the art. For example, the method of the invention may be used in processes involving immobilization of cells, cell components, organelles, viruses or any biological or any other substance having at least one characteristic determinant. Thus the present invention could be beneficially used in the fields of diagnostic and therapeutic medicine, drug testing, gene therapy, in-vitro fertilization, forensic science, as well as food and environmental testing. The invention is, therefore, not limited to the embodiments specifically described and exemplified above, but is capable of variation and modification without departing from the spirit of the invention, the full scope of which is delineated by the appended claims.

What is claimed is:

1. An assay method for determining the presence or quantity of an analyte in a test sample, said analyte having a first binding site and a second binding site, which may be the same or different, at least one of said first and second binding sites comprising a characteristic determinant of said analyte, said assay comprising the steps of:
   a) adding to the test sample i) a signal producing agent comprising a specific binding substance which binds specifically to one of said first or second binding sites of said analyte and ii) a capture agent comprising a specific binding substance which binds specifically to the other of said first or second binding sites of said analyte and which is bonded to magnetic particles or adapted to be bonded to magnetic particles that are introduced into said test sample and wherein said magnetic particles bear one member of a specific binding pair for collection;
   b) subjecting the test sample containing said signal producing agent and said capture agent to conditions causing complex formation between said analyte, said signal producing agent and said capture agent the resulting complex containing said magnetic particles;
   c) contacting said test sample with a collection surface, to which is affixed the other member of said specific binding pair for collection, under the influence of a magnetic field to promote binding interaction between said specific binding pair members, causing said magnetic particle-containing complex to be collected on said collection surface;
   d) separating uncomplexed, signal producing agent from signal producing agent present in said complex; and
   e) detecting signal from said separated signal producing agent present in said complex or from said separated uncomplexed signal producing agent, from which the presence or quantity of said analyte in said test sample is determined.

2. A method as claimed in claim 1, wherein the specific binding substance of said capture agent is adapted to be bonded to said magnetic particles by a specific binding pair for capture, one member of said specific binding pair for capture being conjugated directly or indirectly to the specific binding substance of said capture agent and the other member of said specific biding pair for capture being bonded directly or indirectly to said magnetic particles.

3. A method as claimed in claim 2, wherein at least one of said specific binding pair for collection and said specific binding pair for capture is selected from the group consisting of antigen-antibody, receptor-hormone, receptor-ligand, agonist-antagonist, $F_c$ receptor of IgG-Protein A, $F_c$ receptor IgG-Protein G, $F_c$ receptor of IgG-rheumatoid factor, avidin-biotin, streptavidin-biotin, virus-receptor, lectin-receptor and nucleotide-hybridizing sequences.

4. A method as claimed in claim 2, wherein said specific binding pair for collection and said specific binding pair for capture comprise biotin-streptavidin and biotin is conjugated to the specific binding substance of said capture agent and affixed to said collection surface.

5. A method as claimed in claim 2, wherein said magnetic particles are colloidal particles comprising a magnetic metal compound to which said one member of a specific binding pair for collection and said other member of said specific binding pair for capture are bonded.

6. A method as claimed in claim 2, wherein bonding of said specific binding substance of said capture agent to said magnetic particles occurs during performance of said assay.

7. A method as claimed in claim 6 wherein said conjugate, comprising said specific binding substance of said capture agent and said one member of said specific binding pair for capture, and said magnetic particle-bonded other member of said specific binding pair for capture are added sequentially to said test sample and subjected to conditions causing binding of the members of said specific binding pair for capture.

8. A method as claimed in claim 1, wherein said specific binding substance of said capture agent is bonded to said magnetic particles.

9. A method as claimed in claim 1, wherein a substantially uniform thickness of magnetic particle-containing complex is collected on said collection surface.

10. A method as claimed in claim 9, including the step of washing said magnetic particle-containing complex in situ on said collection surface.

11. A method as claimed in claim 9, including the step of detecting signal from, signal producing agent present in said magnetic particle-containing complex in situ on said collection surface.

12. A method as claimed in claim 1, wherein a particulate analyte is determined, each of said first and second binding sites of said particulate analyte comprises a distinct characteristic determinant of said analyte, and each of said signal producing agent and said capture agent bind to a different one of said distinct characteristic determinant of said analyte.

13. A method as claimed in claim 2, wherein said specific binding pair for collection and said specific binding pair for capture comprise the same two members, and the same member of said specific binding pair is conjugated to said capture agent and affixed to said collection surface.

14. A method as claimed in claim 1, wherein said signal producing agent comprises a signal producing substance selected from the group consisting of molecules or ions directly or indirectly detectable based on light absorbance, fluorescence, phosphorescence, or luminescence properties; molecules or ions detectable by their radioactive properties; and molecules or ions detectable by their nuclear magnetic resonance or paramagnetic properties.

15. A method as claimed in claim 1, wherein said signal producing agent comprises an enzyme-bound antibody.

16. A method as claimed in claim 1, wherein the other member of said second specific binding pair is affixed to the interior surface of a micro-titre well.

17. In an analytical method comprising collecting analyte-bearing magnetic particles from a test sample in a receptacle having a collection surface, wherein a treatment solution is deposited in said receptacle in an amount sufficient to submerge said collected analyte-bearing magnetic particles and said treatment solution is evacuated from said receptacle, the improvement which comprises directly or indirectly bonding to said magnetic particles one member of a specific binding pair, directly or indirectly affixing to said collection surface the other member of said specific binding pair and contacting said collection surface with said test sample under the influence of a magnetic field to promote binding interaction between said specific binding pair members and cause binding of said analyte-bearing magnetic particles to said collection surface, whereby said analyte-bearing magnetic particles are maintained in place on said collection surface, without appreciable displacement caused by the depositing or evacuation of said treatment solution.

18. A method as claimed in claim 17, wherein said analyte-bearing magnetic particles are dissociably bound to said collection surface.

19. A method as claimed in claim 18, wherein said analyte-bearing magnetic particles are dissociated from said collection surface and caused to undergo at least one reaction with a biological assay agent.

20. A method as claimed in claim 19, wherein said biological assay agent is a signal producing agent.

21. A method as claimed in claim 17, wherein a substantially uniform thickness of said analyte-bearing magnetic particles is collected and maintained in place on said collection surface.

22. A method as claimed in claim 17, wherein said one specific binding pair member is directly bonded to said magnetic particles and said other specific binding pair member is directly affixed to said collection surface.

23. A method as claimed in claim 17, wherein an interior surface of said receptacle constitutes said collection surface.

24. An assay method for determining the presence or quantity of an analyte in a test sample, said analyte having a first binding site and a second binding site at least one of said first and second binding sites comprising a characteristic determinant of said analyte, said assay being carried out in at least two stages, including a first stage comprising the steps of:

a) adding to the test sample a capture agent comprising one member of a first specific binding pair for capture and a binding substance that binds selectively to one of said first or second binding sites of said analyte;

b) subjecting the test sample containing said capture agent to conditions causing complex formation between said analyte and said capture agent;

c) contacting the formed complexes with magnetic particles bearing the other member of said first specific binding pair for capture and one member of a second specific binding pair for collection, the amount of said magnetic particles being in excess of that required to bind said formed complexes, under conditions causing binding of the members of said first specific binding pair, the resulting complexes containing said magnetic particles;

d) contacting said test sample with a collection surface to which is affixed the other member of said second specific binding pair for collection, under the influence of a magnetic field to promote binding interaction between magnetic particle-containing complexes and the other member of said second specific binding pair, causing said magnetic particle-containing complexes to be collected on said collection surface; and e) separating magnetic particle-containing complexes from said test sample; and a second stage comprising the steps of:

f) contacting said magnetic particle-containing complexes with a signal producing agent comprising a specific binding substance that binds specifically to the other of said binding sites of said analyte under conditions causing binding of said signal producing agent to analyte present in said magnetic particle-containing complexes;

g) separating unbound signal producing agent from signal producing agent which is bound to said analyte; and h) detecting signal from said bound signal producing agent, from which the presence or quantity of said analyte in said test sample is determined.

25. A method as claimed in claim 24, wherein a substantially uniform thickness of magnetic particle-containing complexes is collected on said collection surface.

26. A method as claimed in claim 24, wherein said first specific binding pair for capture and said second specific binding pair for collection comprise the same two members, and the same member of said specific binding pair is conjugated to said capture agent and affixed to said collection surface.

27. A method as claimed in claim 24, wherein said first specific binding pair for capture and said second specific binding pair for collection comprise biotin-streptavidin and biotin is conjugated to said capture agent and affixed to said collection surface.

28. A method as claimed in claim 24, wherein said magnetic particles are colloidal particles comprising a magnetic metal compound to which the other member of said first specific binding pair for capture and the one member, of said second specific binding pair for collection are bonded.

29. A method as claimed in claim 24, wherein said magnetic particle-containing complexes are dissociably collected on said collection surface in said first stage.

30. A method as claimed in claim 29, wherein said particle-containing complexes are dissociated from said collection surface prior to said second stage, contacted in a dissociated condition with said signal producing agent in said second stage and thereafter collected on said collection surface by binding of said second specific binding pair members.

31. A method as claimed in claim 24, wherein said analyte is an antibody, said binding substance of said capture agent is an anti-isotypic antibody which binds selectively to the Fc binding site of said antibody analyte and said specific binding substance of said signal producing agent is antigen that binds specifically to the Fc binding site of said antibody analyte.

32. A method as claimed in claim 24, wherein said analyte is IgM, said binding substance of said capture agent is anti-IgM, and said specific binding substance of said signal producing agent is selected from the group consisting of antigenic determinants of hepatitis, Human Immunodeficiency Virus (HIV), Rubella, Chlamydia, Toxo and Cytomegalo Virus.

33. An assay method for determining the presence or quantity of an analyte in a test fluid, said analyte having a first binding site and a second binding site, at least one of said first and second binding sites comprising a characteristic determinant of said analyte, said assay being carried out in at least two stages, including a first stage comprising the steps of:

a) adding to the test fluid a capture agent comprising one member of a first specific binding pair for capture and a binding substance that binds selectively to one of said first or second binding sites of said analyte;

b) subjecting the test fluid containing said capture agent to conditions causing complex formation between said analyte and said capture agent;

c) contacting the formed complexes with magnetic particles bearing the other member of said first specific binding pair for capture and one member of a second specific binding pair for collection, the amount of said magnetic particles being in excess of that required to bind said formed complexes, under conditions causing binding of the members of said first specific binding pair, the resulting complexes containing said magnetic particles;

d) contacting said test fluid with a collection surface to which is affixed the other member of said second specific binding pair for collection, under the influence of a magnetic field to promote binding interaction between magnetic particle-containing complexes and the other member of said second specific binding pair, causing said magnetic particle-containing complexes to be collected on said collection surface; and e) separating magnetic particle-containing complexes from said test fluid; and a second stage comprising the steps of:

f) providing said magnetic particle-containing complexes in a non-magnetic fluid phase;

g) contacting said magnetic particle-containing complexes on said collection surface with a solution containing a non-magnetic signal producing agent, which comprises a specific binding substance that binds specifically to the other of said binding sites of said analyte, and a quantity of colloidal magnetic particles, and solution forming a distinct phase in said non-magnetic fluid phase, the magnetic and non-magnetic components of said solution being stably confined within said distinct phase;

h) imposing in the vicinity of said collection surface of a magnetic field having a region of sufficiently high intensity to cause said distinct phase to be positioned adjacent to said collection surface;

i) allowing the specific binding substance of said signal producing agent to bind to analyte present in said magnetic particle-containing complexes;

j) separating unbound signal producing agent from signal producing agent which is bound to said analyte; and k) detecting signal from said bound signal producing agent, from which the presence or quantity of said analyte in said test sample is determined.

34. A method as claimed in claim 33, wherein a substantially uniform thickness of magnetic particle-containing complexes is collected on said collection surface in said first stage.

35. A method as claimed in claim 33, wherein a particulate analyte is determined, each of said first and second binding sites of said particulate analyte comprises a distinct characteristic determinant of said analyte, and each of said signal producing agent and said capture agent bind to a different one of said distinct characteristic determinant of said analyte.

36. A method as claimed in claim 33, wherein said first specific binding pair for capture and said second specific binding pair for collection comprise the same two members, and the same member of said specific binding pair is conjugated to said capture agent and affixed to said collection surface.

37. A method as claimed in claim 33, wherein the magnetic particles that are contacted with the complexes formed in said first stage are colloidal particles comprising a magnetic metal compound to which the other member of said first specific binding pair for capture and the one member of said second specific binding pair for collection are bonded.

38. A method as claimed in claim 37 wherein the magnetic particles that are contacted with the complexes formed in said first stage are of larger size than magnetic particle component of said solution.

39. A method as claimed in claim 8, wherein at least one member of said specific binding pair for collection is caused to assume a conformation that inhibits binding between the members of said specific binding pair for collection; and after complex formation and prior to collection of said magnetic particle-containing complex on said collection surface the cause of said binding inhibiting conformation is eliminated and binding occurs between said members.

* * * * *